United States Patent [19]
Landauer

[11] Patent Number: 5,974,678
[45] Date of Patent: Nov. 2, 1999

[54] INFANTOMETER FOR MEASURING HEIGHT OF INFANTS

[75] Inventor: Konrad S. Landauer, Chicago, Ill.

[73] Assignee: Clover Global Group, Inc., Chicago, Ill.

[21] Appl. No.: 08/967,809

[22] Filed: Nov. 12, 1997

[51] Int. Cl.[6] .............................. G01B 3/02; G01B 5/02
[52] U.S. Cl. .............................. 33/512; 33/806; 33/515
[58] Field of Search .......................... 33/512, 783, 806, 33/809, 810, 811, 511, 515

[56] References Cited

U.S. PATENT DOCUMENTS

| | | | |
|---|---|---|---|
| 1,555,792 | 9/1925 | Souder | 33/810 |
| 3,492,737 | 2/1970 | Swanson | 33/809 |
| 4,939,849 | 7/1990 | Johnson | 33/512 |
| 5,097,617 | 3/1992 | Craven | 33/511 |
| 5,499,457 | 3/1996 | Weiler et al. | 33/512 |

FOREIGN PATENT DOCUMENTS

| | | | |
|---|---|---|---|
| 770829 | 9/1934 | France | 33/512 |

OTHER PUBLICATIONS

Seca Corp. product literature on Infantometers and Scales (Date unknown).

Primary Examiner—Christopher W. Fulton
Attorney, Agent, or Firm—Milton S. Gerstein

[57] ABSTRACT

An infantometer is made of low-friction styrene, has two telescoping halves, with each having half of the measuring indicia thereon. The first stationary half has a fixed handle against which the head of the infant is placed. The measuring indicia or scale on the first half is located along one side edge thereof. The second, sliding half telescopingly slides in the first fixed half, and has a fixed foot-handle attached at it distal, free end for abutment against the feet of the out-stretched infant. The measuring indicia or scale on the second half is located along a side edge thereof laterally opposite to that corresponding to the first half. The measuring indicia on the second half is arranged in descending order of magnitude, so that the free end-edge of the first half serves as a indication-rule. The two halves have an upper surface that form a trough or concave central section on which the infant is supported, whereby the infant is prevented from falling out.

16 Claims, 4 Drawing Sheets

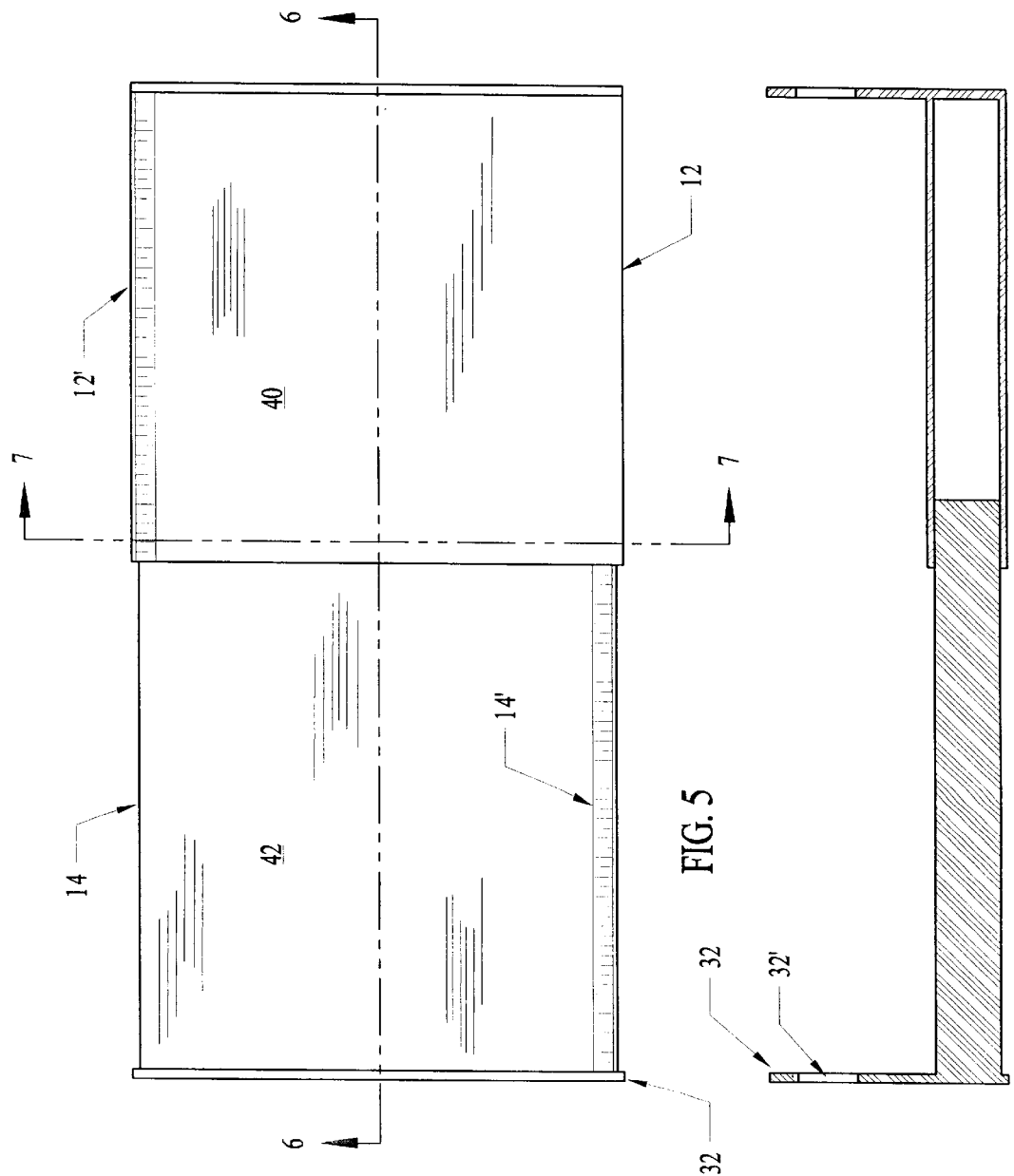

INFANTOMETER FOR MEASURING HEIGHT OF INFANTS

BACKGROUND OF THE INVENTION

The present invention is directed to a mechanical device for measuring the height of infants up to thirty-seven inches, which is typically the height of a two-year old. It is, in some cases, extremely critical to be able to measure the height of an infant accurately, with very little margin of error tolerated, for those infants requiring the periodic administering of human growth hormone, or HGH. The amount of dosage of HGH, as well as the change in any dosage, is dependent upon the measured height of the infant initially, and the differential growth rates thereafter. By being able to obtain a substantially exact measurement of the height of the infant, the dosage to be administered may be more fine-tuned, thus preventing over-dosaging or under-dosaging, either of which may have potentially adverse effects on the infant. A measurement that is off by one-quarter inch can affect the determination of the amount of HGH to be administered.

There are presently used mechanical infantometers that are used to measure the infant's height. However, they suffer from a number of drawbacks and disadvantages. A first type sold by Seca Corp. is made of vinyl or rubber which is unfolded during use. There is a measuring scale imprinted on the face of the unit, with upstanding head and foot plates being used to provide the reading. The problem with this infantometer is that it requires two persons, one to hold the infant still, and the other to do the actual measuring. In addition, this type of infantometer must be unfolded and stretched out, and, since it is made of vinyl or rubber, any stretching thereof will distort the measurement, since the imprinted indicia lines of the scale on the face of the unit will be stretched greater or closer apart depending upon how much the unit is stretched. This will, therefore, invariably result in a less exact reading. Moreover, the stretching of the unit will sometimes cause the edges thereof to curl, also resulting in a skewed reading. Moreover, the infant often tends to stick to the rubber or vinyl, making it difficult to position and reposition the infant as necessary.

In a second type of infantometer also sold by Seca Corp., instead of rubber or vinyl being used, wood is used instead. In this type, the infantometer does not require unfolding, and has scales on the edges thereof, with one sliding foot-plate being moved to indicate the indicia indicative of the height of the infant. There is also provided a fixed head-plate against which the infant's head is placed. This type also suffers from the disadvantage of requiring two persons, one to hold the baby to ensure he or she does not fall off, and a second to do the actual measuring. Moreover, another drawback of this type of infantometer is that it is ofttimes difficult or cumbersome to slide the sliding foot-plate to indicate the measurement, since the part that mounts the foot-plate to the wooden base also serves as a support that helps to support the infantometer on a flat surface; thus, when sliding the foot-plate, both static and dynamic friction must be overcome, which, by itself, can lead to an errant measurement.

SUMMARY OF THE INVENTION

It is, therefore, the primary objective of the present invention to provide a mechanical infantometer that overcomes all of the disadvantages and drawbacks of the prior-art mechanical infantometers.

It is a primary objective of the present invention to provide an infantometer that safely supports an infant thereon without the need of a person holding the baby, whereby only one person is needed to use the infantometer of the invention, in contradistinction to the prior-art infantometers that require two persons.

It is another primary objective of the present invention to provide an improved mechanical infantometer that provides a more exact measurement of the height of an infant by reducing friction of sliding parts.

It is another primary objective of the present invention to provide an improved mechanical infantometer that allows for a quicker measurement of the height of an infant.

Toward these and other ends, the infantometer, in the preferred embodiment of the present invention, is made of styrene, and has two telescoping halves, with each having measuring indicia thereon. The first stationary half has a fixed head-plate against which the head of the infant is placed. The measuring indicia or scale on the first half is located along one side edge thereof. The second, sliding half telescopingly slides in the first fixed half, and has a fixed foot-plate attached at it distal, free end for abutment against the feet of the outstretched infant. The measuring indicia or scale on the second half is located along a side edge thereof laterally opposite to that corresponding to the first half. The two halves have an upper surface that form a trough or concave central section on which the infant is supported, whereby the infant is prevented from escaping or falling out. The bottom surface of both halves may also define curved side edges to reduce frictional surface-to-surface contact, which friction is further reduced owing to the fact that the infantometer is made of low-coefficient-of-friction styrene.

BRIEF DESCRIPTION OF THE DRAWINGS

The invention will be more readily understood with reference to the accompanying drawing, wherein:

FIG. 5 is a top view thereof;

FIG. 6 is a cross-sectional view taken along line 6—6 of FIG. 5;

DETAILED DESCRIPTION OF THE INVENTION

Figure 1:
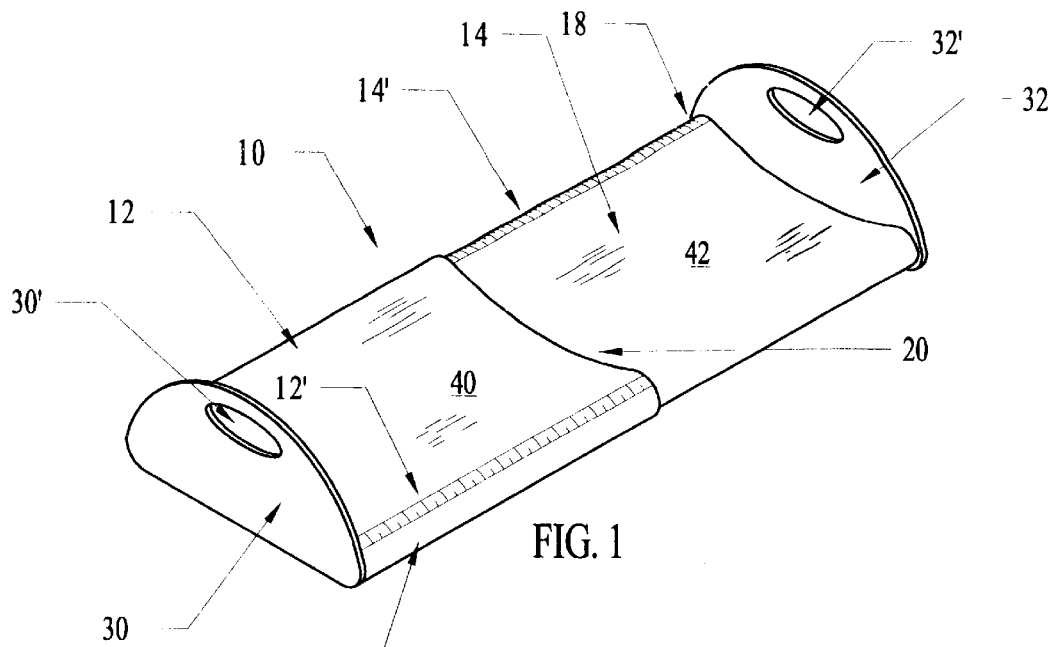
FIG. 1 is an isometric view of the infantometer of the invention.
Figure 2:
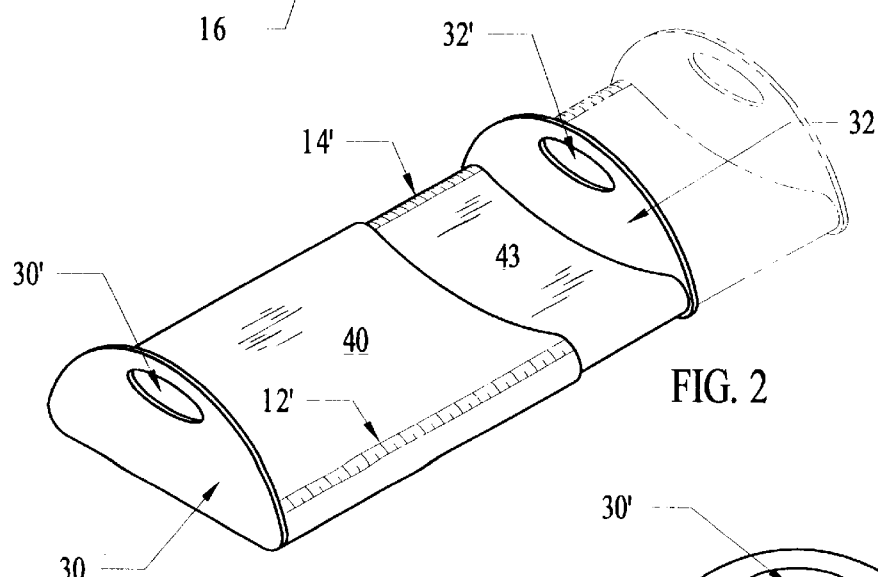
FIG. 2 is an isometric view of the infantometer showing the variable positioning thereof for measuring the height of an infant.
Figure 4:
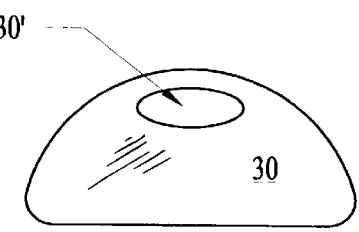
FIG. 4 is an end view thereof.
Figure 3:
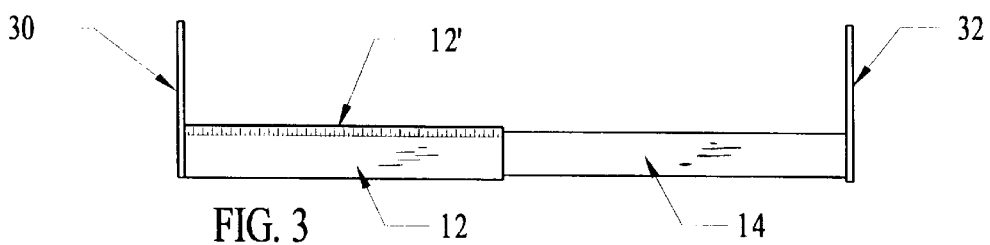
FIG. 3 is a side view thereof.

Referring now to the drawings in greater detail, and to FIGS. 1–7 for now, there is shown the preferred embodiment 10 of the infantometer of the invention. The infantometer 10 is made up of two relatively sliding halves or parts 12, 14, each being preferably made of a low friction thermoplastic such as styrene. The first half or part 12 telescopingly receives therein the second half or part 14. Each half 12, 14 is provided with half of a linear ruler or scale. The first half has a lower scale-half 12' running from between 1 and 17 inches. The scale-half 12' is located along one lateral side edge 16. The second half has an upper, second scale-half 14' running from between 37 and 17 inches. The upper, second scale-half 14' is located along one lateral side edge 18, parallel to but laterally opposite relative to the side edge 16 containing the first scale-half. The first scale-half 12' extends normally and in ascending order of magnitude, with the greatest value, such as 17 inches, being located at the transverse edge-surface 20 of the first half 12. In contrast, the upper, second scale-half 14' starts with its greatest value, such as 37 inches, at its transverse edge 22, and decreases in value in direction along lateral edge 14' away from the first part or half 12. This is so, so that when the tallest infant is being measured, the transverse edge-surface 20 of the first half 12 acts as an index to indicate the measurement. The reason why the first scale-portion goes up to 17 inches is that a new born is usually greater than 17 inches, and the reason why second half stops at 37 inches is that at that age two the baby can usually walk, and, therefore, may be measured by a standard statiometer.

Figure 7A:
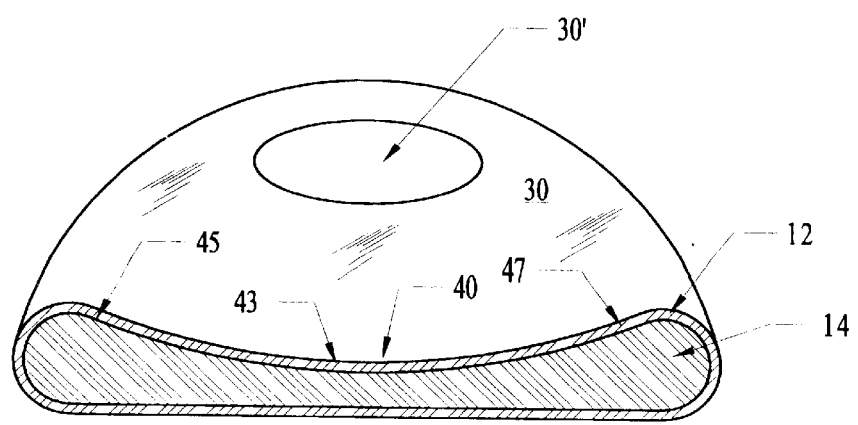
FIG. 7A is a cross-sectional view taken along line 7—7 of FIG. 5.

Each half or part 12, 14 has an upstanding handle 30, 32, respectively, with an opening 30', 32', respectively, for allowing a hand to grip the handle, in order to slidingly open or close the two sliding parts 12, 14, in order to measure an infant, and which allows the device to be opened up by just one person. The holes also allow the device to be carried easily. The handle 32 has a lower or bottom surface 34 that protrudes downwardly a slight amount below the bottom surface of the second half 14, as best seen in FIG. 6, which protrusion is approximately the same as the thickness of the lower or bottom surface 36 of the first part or half 12, so that the device 10 is supported on a support surface evenly. This considerably reduces the friction as the second part 14 is slid in or out. Also, the bottom of the handle 32 may be slightly concave-shaped so that only the lateral ends of the bottom surface of the handle 32 contacts the support surface therebelow. In addition, the bottom or lower surface of the first part or half 12 may be slightly concave, as seen in FIG. 7A, so that frictional contact with the supporting surface therebelow occurs along the central portion of the bottom or lower surface 36. Preferably, the bottom surface 36 has a straight middle section of between five and seven inches that contacts the supporting surface therebelow, with the bottom surface thereafter curving upwardly to form upwardly curved side walls, described hereinbelow.

Figure 7B:
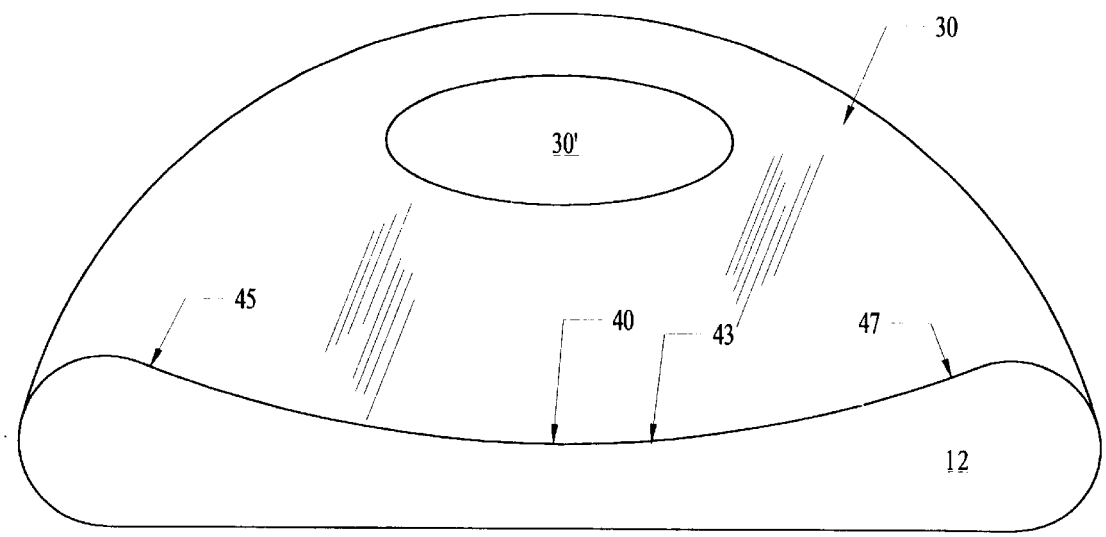
FIG. 7B is an end view of the first part of the infantometer showing the upper, concave supporting surface thereof.

The upper surface 40, 42 of the first and second halves 12, 14, respectively, is slightly concave-shaped or arcuate in order to prevent the infant from falling off. Thus, the measurement of the height of the infant may be performed by just one person, since there is no requirement of another person holding the infant down to prevent his or her falling off. In the preferred embodiment, as can be seen in FIGS. 7A and 7B, the upper surface 40 or 42 defines a concave-shaped surface that defines a top surface 43 with upwardly-inclined side walls 45, 47. Each side wall 45, 47 defines an initial section joined to the top surface 43; the initial sections, and therefore the width of the top surface 43, are spaced about eight inches apart, in the preferred embodiment, which is the minimum distance between the two shoulder blades of the smallest infant to be measured by the device 10. For larger infants, with shoulder blades spaced farther apart, higher elevations along the concave, curved side walls are used to support the shoulder blades. It is important that the shoulder blades are supported, and not the shoulders, in order to obtain an accurate reading by keeping the baby well-supported and stationary on the device via the support of the shoulder blades. In the preferred embodiment, the maximum height of each side wall, at the extreme edge, is about 2.2108 inches, while the overall width of device is 12.0117 inches. The infantometer 10 is used to measure infants up to 37 inches tall, which is about two years of age. the overall length of the device is about 38 inches.

Figure 8:
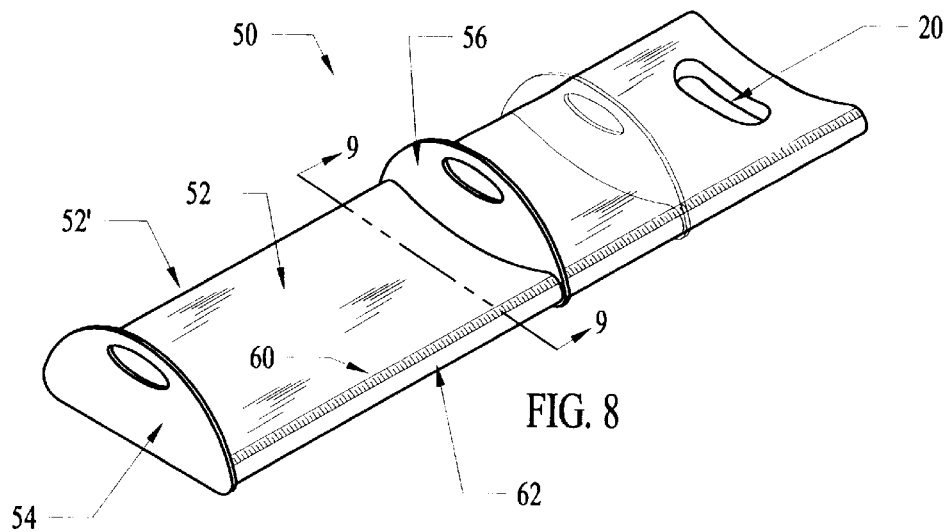
FIG. 8 is an isometric view of a second embodiment of the infantometer of the invention.
Figure 9:
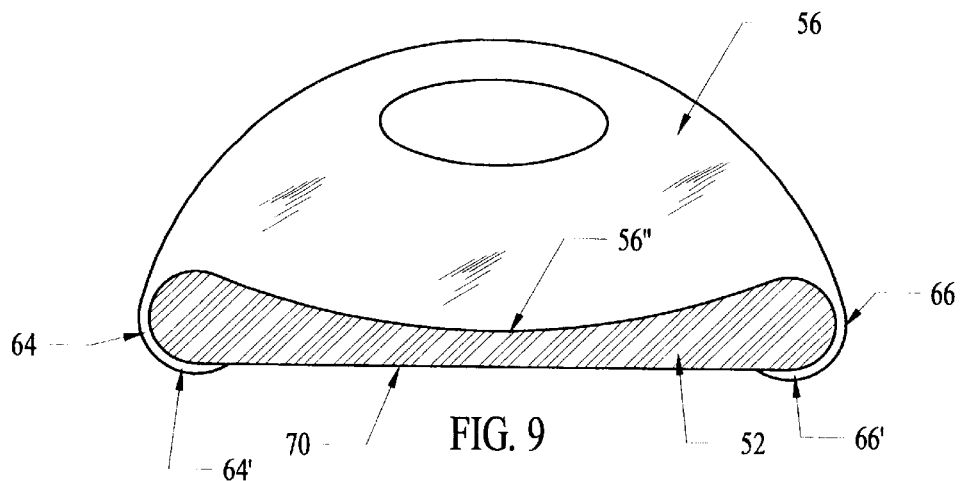
FIG. 9 is a cross-sectional view taken along line 9—9 of FIG. 8.

In FIGS. 8 and 9, there is shown a second embodiment 50 of the infantometer, also made preferably of styrene. In this embodiment, there are no sliding halves, but rather one main plate 52 having one fixed handle 54 at one end 52', and a slidable handle 56 that is movable along the main plate. The main plate has imprinted, or otherwise laid, a scale 60 running sequentially from 1 to 37 inches. The scale 60 is located along one lateral edge surface 62 of the main plate. The upper surface of the main plate 52 is concave like that of the two halves of the first embodiment, for the same reasons indicated there. The movable handle 56 defines arcuate end-regions 64, 66 that wrap around respective side edges of the main plate 52 for securing the handle thereto yet permitting sliding movement. These arcuate end-regions also define supports 64', 66' which support the handle, and, therefore, the main plate on a supporting surface, to thereby minimize surface contact therebetween, to thus reduce friction, whereby it is easier to move or slide the handle 56 for measuring the infant. The slidable handle 56 also has a convex-shaped lower surface 56" that is contoured to the concave-shape of the upper surface of the main plate 52. This convex-shaped lower surface 56" serves as an indicator on the scale 60 for reading the indicia of the scale for determining the height of the infant laid therealong. The stationary handle 54 may also have a downwardly protruding section below the lower or bottom surface 70 of the main plate approximately equal to the thickness of the supports 64', 66' similar to the handle on the movable half 14 of the first embodiment of FIG. 1. The movable handle 56 is also provided with an opening for receiving the hand for gripping thereby, in order to side the handle to the appropriate position for measuring. The main plate also has an opening 70 at one end thereof, remote from the end thereof that mounts the fixed handle 54, by which the infantometer 50 may be carried and transported.

Figure 10:
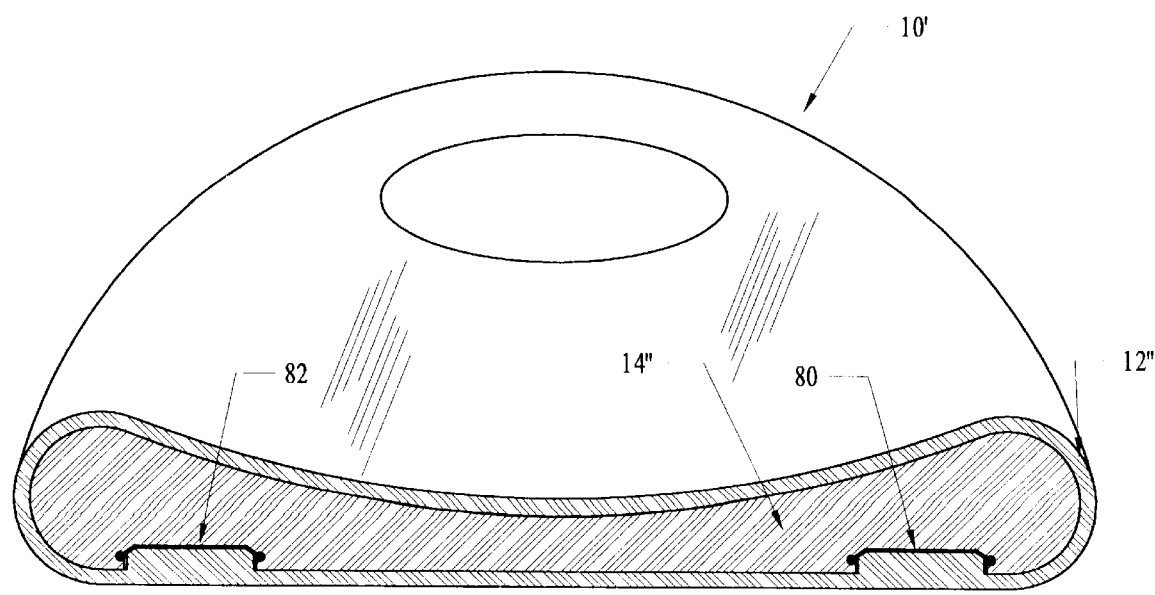
FIG. 10 is a cross-sectional view similar to FIG. 7 with the addition of ball bearings to aid in the reduction of friction.

Referring now to FIG. 10, there is shown a modification of the first embodiment. In this modification 10', the first stationary half or part 12" includes ball bearing mounts 80, 82 on each lateral side, by which the inner, slidable half or part 14" is mounted for basically friction-free movement.

While specific embodiments of the invention have been shown and described, it is to be understood that numerous changes and modifications may be made therein without departing from the scope, spirit and intent of the invention as set forth in the appended claims.

What I claim is:

1. An infantometer for measuring the height of an infant, comprising:

a main body portion having an upper substantially concave-shaped surface for safely receciving and retaining an infant, and a and second end;

scale means on said main body portion for indicating the height of an infant placed on said main body portion;

first handle means mounted to said main body portion at said first end; and second handle means movable relative to said first handle cleans for sliding movement toward and away from said first handle means along said main body portion in a direction between said first and second ends;

said main body portion comprising a first and a second telescoping part, one of said first and second telescoping parts being slidingly received in the other of said first and second telescoping parts for sliding movement therein; said first telescoping part having a first end constituting said first end of said main body portion, and a second end; and said second telescoping part having a first end for sliding movement toward and away from said first end of said first telescoping part, and a second end constituting said second end of said main body portion;

said first handle means being fixedly mounted to said first telescoping part at said first end thereof;

said second handle means being fixedly mounted to said second telescoping part at said second end thereof;

said scale means comprising a first scale section located on said first telescoping part, and a second scale section located on said second telescoping part.

2. The infantometer for measuring the height of an infant according to claim 1, wherein said first scale section comprises first indicia means, and said second scale means comprises second indicia means; said second indicia means extending, in a direction from said first end of said second telescoping part toward said second end of said second telescoping part, in descending order of magnitude;

each of said first and second telescoping parts having a lateral edge surface; said first scale section being located at said lateral edge surface of said first telescoping part, and said second scale section being located at said lateral edge surface of said second telescoping part, said lateral edge surface of said second telescoping part being diametrically opposite to said lateral side edge of said first telescoping part.

3. The infantometer for measuring the height of an infant according to claim 2, wherein said first indicia means extends, in a direction from said first end of said first telescoping part toward said second end of said first telescoping part, in ascending order of magnitude.

4. The infantometer for measuring the height of an infant according to claim 3, wherein said second end of said first telescoping part serves as an indicia indicator for indicating a reading on said second indicia means of said second scale section.

5. The infantometer for measuring the height of an infant according to claim 2, wherein said first telescoping part comprises bearing means in which said first telescoping part moves, in order to reduce the friction between said first and second parts during the relative sliding movement therebetween.

6. The infantometer for measuring the height of an infant according to claim 1, wherein said concave-shaped upper surface for supporting an infant comprises a top surface and a pair of oppositely disposed side walls projecting upwardly from said top surface.

7. The infantometer for measuring the height of an infant according to claim 6, wherein each of said pair of oppositely disposed side walls comprises an initial section connected to said top surface; said initial sections, and therefore the width of said top surface, being spaced apart a distance that supports the shoulder blades of the smallest infant to be measured by said infantometer.

8. The infantometer for measuring the height of an infant according to claim 7, wherein said distance is approximately equal to eight inches.

9. The infantometer for measuring the height of an infant according to claim 1, wherein each of said first and second telescoping parts comprises a bottom surface; said bottom surface of at least said first telescoping part having a central arcuate section that contacts a support surface upon which said infantometer rests.

10. The infantometer for measuring the height of an infant according to claim 9, wherein said second handle means comprises a downwardly projecting portion that extends below said bottom surface of said second telescoping part; said bottom wall of said first telescoping part having a thickness; said downwardly projecting portion extending approximately a distance equal to said thickness of said bottom surface of said first telescoping part.

11. The infantometer for measuring the height of an infant according to claim 1, wherein each of said first and second handle means comprises an opening by which a hand may grip the respective said handle means for moving the respective said parts relative to each other and for carrying said infantometer.

12. The infantometer for measuring the height of an infant according to claim 1, wherein said second handle means comprises an opening by which a hand may grip said second handle means for moving said second handle means relative to said first handle means.

13. In an infantometer for measuring the height of an infant comprising a main body portion, a first handle means, a second handle means movable relative to said first handle means, and scale means on said main body portion, the improvement comprising:

said main body portion having an upper substantially concave-shaped surface for safely receiving and retaining an infant;

said concave-shaped upper surface supporting an infant by supporting the shoulder blades along diametrically opposite locations of said concave-shaped upper surface;

said main body portion comprising a first and a second telescoping part, said second telescoping part being received in said first telescoping part for sliding movement therein, said first telescoping part having a first end and a second end, and said second telescoping part having a first end for sliding movement toward and away from said first end of said first telescoping part, and a second end;

said second handle means being fixedly mounted to said second telescoping part at said second end thereof;

said scale means comprising a first scale section located on said first telescoping part adjacent a lateral side edge thereof, and a section located on said second telescoping part adjacent a lateral side edge thereof diametrically opposite to said lateral side edge of said first telescoping part.

14. The infantometer for measuring the height of an infant according to claim 13, wherein said first scale section comprises first indicia means, and said second scale means comprises second indicia means; said second indicia means extending, in a direction from said first end of said second telescoping part toward said second end of said second telescoping part, in descending order of magnitude.

15. The infantometer for measuring the height of an infant according to claim 14, wherein said second end of said first telescoping part serves as an indicia indicator for indicating a reading on said second indicia means of said second scale section.

16. The infantometer for measuring the height of an infant according to claim 13, wherein said concave-shaped upper surface for supporting an infant comprises a top surface and a pair of oppositely disposed side walls projecting upwardly from said top surface; each of said pair of oppositely disposed side walls comprises an initial section connected to said top surface; said initial sections, and therefore the width of said top surface, being spaced apart a distance that supports the shoulder blades of the smallest infant to be measured by said infantometer.

* * * * *